United States Patent [19]

Nordin

[11] Patent Number: 4,940,409

[45] Date of Patent: Jul. 10, 1990

[54] METHOD AND APPARATUS FOR MAKING DENTAL JAW MODELS

[76] Inventor: Harald E. Nordin, Villa Amphion, CH-1822 Chernex, Switzerland

[21] Appl. No.: 410,024

[22] Filed: Sep. 20, 1989

Related U.S. Application Data

[63] Continuation of Ser. No. 30,031, Mar. 25, 1987, abandoned.

[30] Foreign Application Priority Data

Mar. 27, 1986 [EP] European Pat. Off. ......... 86810149.4

[51] Int. Cl.⁵ ............................................. A61C 19/00
[52] U.S. Cl. ......................................... 433/74; 433/34
[58] Field of Search ..................................... 433/74, 34

[56] References Cited

U.S. PATENT DOCUMENTS

| | | | |
|---|---|---|---|
| 3,498,580 | 3/1970 | Wilson | 433/74 |
| 3,553,839 | 1/1971 | Gores | 433/74 |
| 4,238,189 | 12/1980 | Tirino | 433/74 |
| 4,363,625 | 12/1982 | Avaessian | 433/74 |
| 4,371,339 | 2/1983 | Zeiser | 433/74 |
| 4,449,931 | 5/1984 | Saito | 433/34 |

FOREIGN PATENT DOCUMENTS

| | | |
|---|---|---|
| 0126850 | 12/1984 | European Pat. Off. . |
| 1088188 | 9/1960 | Fed. Rep. of Germany ........ 433/74 |
| 2125927 | 12/1971 | Fed. Rep. of Germany . |
| 2092058 | 8/1982 | United Kingdom . |

Primary Examiner—John J. Wilson
Attorney, Agent, or Firm—Marks Murase & White

[57] ABSTRACT

Tooth and jaw models comprise a base and removable tooth sections which are fastened removably by pins put into suitable holes in the base. After the production of the jaw replica positive a hole is drilled in each section of the positive and the upper parts of the pins are cemented into the holes. The positive, including the pins, is then put into a casting mold having a height equal to the length of the insertion parts of the pins. The casting mold is then filled with gypsum, so that after cutting the positive into section, the sections are non-rotatably but removably fastened in the base and can be separated easily at the visible ends of said insertion parts of the pins.

The pins have a cylindrical upper part and a profiled insertion part having a cross-shaped, star-shaped or triangular section. The prongs of the insertion parts have edges arranged parallel to one another.

The method and apparatus allow a simplified production of tooth models, maintaining the required precision and easy separation of the individual sections from the base.

17 Claims, 1 Drawing Sheet

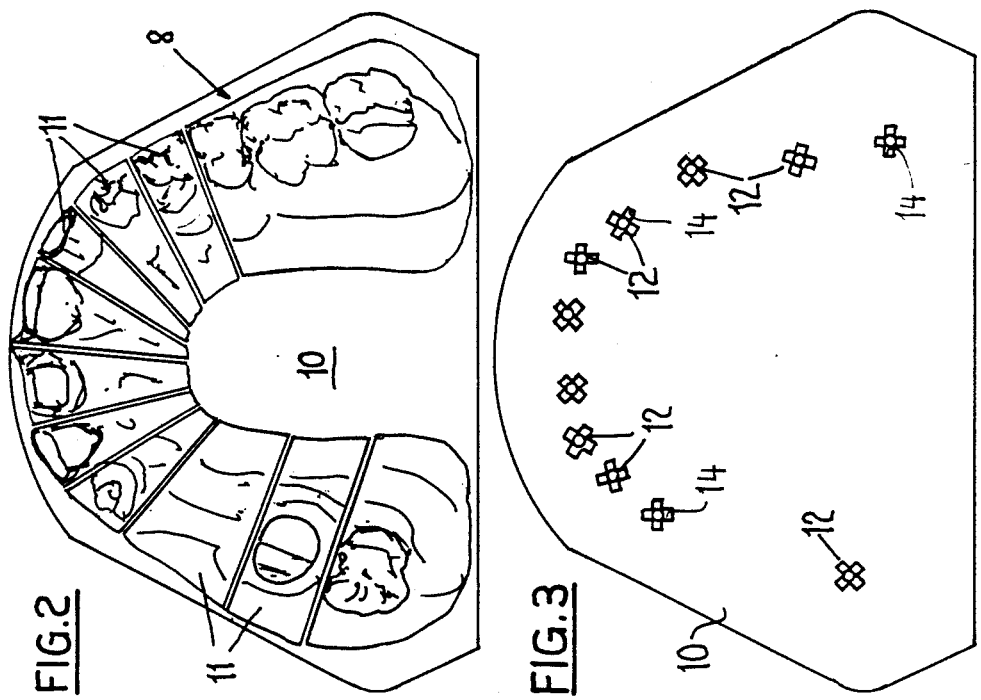
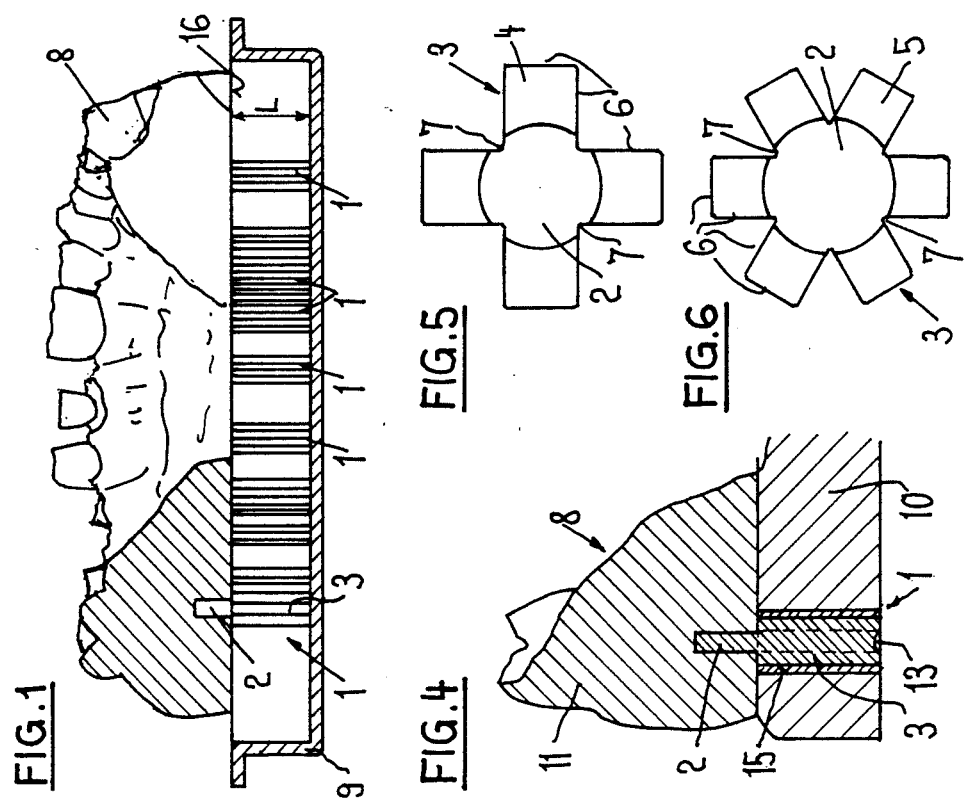

METHOD AND APPARATUS FOR MAKING DENTAL JAW MODELS

BACKGROUND OF THE INVENTION

The present invention refers to a method for making dental and jaw models. The models comprise a base section and removable tooth or casting mold section which are removably secured by pins put into suitable holes in the base.

German Patent No. 2,125,927 discloses method, for making dental models whereby at least two pins are used for every section on the one hand and on the other hand A variant to the two pin method provides no means for easily separating the sections from the base. At the time of filing of German Patent No. 2,125,927 the provision of two pins brought some advantages with reference to the then known prior art by achieving a better guide and a more exact insertion of the tooth sections, whereby a bushing is provided for each pin. Two disadvantages of the method of German Patent No. 2,125,927 are the costs for the material it is therefor to parallelly guide exactly and the two corresponding holes.

German Patent No. 1,088,188 refers to a device for non-rotatably and interchangeably fastening a single supporting pin for a single artificial tooth in a working model. The reference discloses single teeth replacement parts which are fastened removably with a single pin in the working model. All disclosed pins are conical, and have a section departing from the circular form, e.g. a square, triangular or multiangular section. The use of pins with such a cross-section prevents rotation. However, the use of method conical pins introduces the danger that gypsum particles, which can pass between the two conical surfaces of the pin and the hole respectively, will impair the accuracy and the seat.

While pulling out a tooth section from the base for the first time after casting, difficulties can arise and lead to the need for the use of a great force. For solving this problem, the U.S. Pat. No. 3,498,580 proposes to provide the base with window-shaped openings, in which a tool can be inserted for lifting off each tooth section. This brings an additional complication for the production of the base and the model, and a weakening of the base.

SUMMARY OF THE INVENTION

It is therefore the object of the present invention to disclose a method and a means for carrying out the method whereby tooth and jaw models can be produced in a simplified manner, in which each section is rotatably and securely fastened to yet easily separable from, the base of the model.

Further objects and advantages of the invention will be apparent from the following description, taken in connection with the accompanying drawings.

BRIEF DESCRIPTION OF THE DRAWINGS

FIG. 1 is a section of a molded tooth model in the mold,

FIG. 2 shows a plan view of the sectionalized tooth model of FIG. 1 from above and mounted on the base, FIG. 3 shows a plan view of the base of the model from below, FIG. 4 is an enlarged sectional of the tooth model in the base and FIGS. 5 and 6 show plan views of two embodiments of a fastening pin from above.

DESCRIPTION OF THE PREFERRED EMBODIMENTS

As will be shown below, the simplified production, maintaining the prevention of rotation and the precision, relies on the use of one single pin for each tooth or mold section, and the facilitated lifting off of the tooth sections from the base relies on the fact that the pin goes through the base, which condition can be easily realized by using a suitable casting mold.

The pin 1 shown in FIGS. 1, 4, and 5 has a cylindrical upper part 2 and a profiled insertion part 3. This profiled insertion part 3 has, as shown in FIGS. 5 and 6, a cross-shaped cross-section 4 or a star-shaped cross-section 5. The cross-shaped cross-section 4 as well as the star-shaped 5 cause a total prevention of rotation; thus it is not necessary to use two pins per tooth section. The edges 6 of each prong of the cross-shaped 4 or star-shaped 5 cross-sections are parallel to each other. This has the advantage that the dust or gypsum particles in the holes are pushed out and thus those particles cannot impair the precision and the seat. It is evident that other cross-sections than above mentioned ones can be used as well, e.g. a triangular cross-section or a star-shaped cross-section with more edges than shown in FIG. 6, can be used. Advantageously, the cylindrical part 2 of the pin is provided with grooves 7 for obtaining a better adhesion in the jaw replica positive. The pins may be comprised of a suitable metal, such as brass For facilitating the separation of the tooth sections from the base, a bushing 15 with a shape corresponding to the shape of the insertion part 3 and made of plastics material can be used.

For the production of the tooth model according to FIG. 1, first the jaw replica positive 8 is made, then its lower surface or base 16 is ground, whereupon the indiviudual sections are traced. Next a hole is drilled in each section and the pins 1 are glued in place with their cylindrical parts 2 using a cement, for example a cyanoacrylate cement. The pins 1 of the positive 8 are then put into a casting mold 9, the clear height of which corresponds to the length L of the profiled insertion part 3. Then the base 10 is formed by pouring gypsum into the mold 9, and at least the individual sections 11 are cut off. Before pouring the gypsum measures should be taken to be able to separate the positive 8 from the casting mold 9 and the pins 1 from the base 10 for which suitable and known separation means are utilized.

Because the clear height of the casting mold 9 corresponds to the length of the insertion parts 3, the ends 12 of the insertion parts are laid open or can be easily laid open as at the most only a very thin layer may obstruct them. Thus the individual sections can be removed easily by pressure on the ends 12. For facilitating the use of a tip it is advantageous to provide the profiled pin ends 12 with an indentation 13, see in particular FIG. 4.

As follows from the description it is not always necessary to use bushings 15 in the base 10, since the insertion part 3 of the pin 1 with the parallel edges allows for good guiding without wear of the openings 14. In this case the production is still more simplified and less material is used.

However, if a better guiding and an easier gliding of the pins 1 in the base 10 is desired, bushings 15 can be used, which are put onto the insertion parts before putting the positive 8 onto the casting mold 9.

It should further be mentioned that by simply placing the pins 1 of the positive 8 into the casting mold 9, the orientation of the insertion parts 3 of the pins 1 no longer matters, which is a further simplification of the production of models.

What I claim:

1. A pin for use in a tooth and jaw model for removably attaching a jaw replica positive severed into a plurality of sections to a base comprising;
  a generally cylindrical first axial portion; and
  a second axial portion of generally constant cross-sectional shape and area, containing a plurality of prongs extending the length of said second axial portion, each prong comprising a plurality of planar faces of which at least two are parallel.

2. The pin of claim 1, wherein said second axial portion further comprises a cross-shaped cross-section.

3. The pin of claim 1, wherein said second axial portion further comprises a star-shaped cross-section.

4. The pin of claim 1, where said second axial portion further comprises an indentation at a terminal face thereof.

5. The pin of claim 1, further comprising a bushing means for receiving said second axial portion for facilitating insertion into the base.

6. The pin of claim 1, wherein said first cylindrical axial portion has a plurality of exterior groove means for improving adhesion with the jaw replica positive section.

7. A tooth and jaw model comprising:
  a jaw replica positive divided into a plurality of sections with each section containing a seat for receiving a pin;
  a plurality of pins, each pin having a cylindrical first axial portion which snugly fits into said seat and a second axial portion of constant cross-sectional shape and area. containing a plurality of prongs extending the length of said second axial portion, each prong comprising a plurality of planar faces of which at least two are parallel, said second axial portion extending downwardly from said seat when said first axial portion is fixed in said seat; and
  a base removably attached to said jaw replica positive by removably receiving the second axial portion of said plurality of pins fixed in said jaw positive, said base having a height equal to the height of said second axial portion.

8. The model of claim 7, wherein said second axial portions further comprises a cross-shaped cross section.

9. The model of claim 7, wherein said second axial portions further comprises a star-shaped cross-section.

10. The model of claim 7, further comprising bushing means for receiving said second axial portion for facilitating insertion into the base.

11. The model of claim 7, wherein said second axial portion further comprises an indentation at a terminal face thereof.

12. The model of claim 7 wherein said first cylindrical axial portion has a plurality of exterior groove means for improving adhesion with said jaw replica positive.

13. The model of claim 7, wherein said first cylindrical axial portion is provided with groove means for improving adhesion with said jaw replica positive.

14. A method of making a tooth and jaw model consisting of a base and tooth and jaw portions comprising the steps of:
  constructing a jaw replica positive;
  forming a seat in each of a plurality of different areas of said jaw replica positive for receiving a pin;
  fixing a pin into each of said seats, each pin having a cylindrical first axial portion which snugly fits into said seat and a second axial portion of constant cross-sectional shape and area, containing a plurality of prongs extending the length of said second axial portion, each prong comprising a plurlity of planar faces of which at least two are parallel, said second axial portion extending downwardly from said seat when said first axial portion is fixed in said seat;
  setting jaw replica positive atop a casting mold, said casting mold having a height equal to the height of said second axial portion;
  filling said casting mold with a casting material to form a base form which the jaw replica positive can be removably fastened; and
  dividing said different areas of said jaw replica positive into a corresponding plurality of sections each containing a seat.

15. The method according to claim 14, wherein said casting material is gypsum.

16. The method according to claim 14, further comprising the step of placing bushing means onto said second axial portion prior to setting said jaw replica positive atop said casting mold.

17. The method according to claim 14, further comprising the step of providing an indentation at a terminal face of said second axial portion.

* * * * *